US008609128B2

(12) United States Patent
Zhang et al.

(10) Patent No.: US 8,609,128 B2
(45) Date of Patent: Dec. 17, 2013

(54) CYANOACRYLATE-BASED LIQUID MICROBIAL SEALANT DRAPE

(75) Inventors: Sheng Zhang, Lenoir, NC (US); Rafael Ruiz, Hudson, NC (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 745 days.

(21) Appl. No.: 12/378,277

(22) Filed: Feb. 12, 2009

(65) Prior Publication Data

US 2010/0112036 A1    May 6, 2010

Related U.S. Application Data

(60) Provisional application No. 61/197,954, filed on Oct. 31, 2008.

(51) Int. Cl.
*A61F 13/00* (2006.01)
(52) U.S. Cl.
USPC .......................................... 424/443; 514/526
(58) Field of Classification Search
None
See application file for complete search history.

(56) References Cited

U.S. PATENT DOCUMENTS

| | | |
|---|---|---|
| 211,104 A | 1/1879 | Mulford |
| 334,046 A | 1/1886 | Pinkham |
| 1,221,227 A | 4/1917 | Shulz |
| 1,229,195 A | 6/1917 | Hamilton |
| 1,234,844 A | 7/1917 | Williams |
| 1,822,566 A | 9/1931 | Davies |
| 2,333,070 A | 10/1943 | Hoey et al. |
| 2,721,858 A | 10/1955 | Joyner et al. |
| 2,794,788 A | 6/1957 | Coover, Jr. et al. |
| 2,912,454 A | 11/1959 | McKeever |
| 3,152,352 A | 10/1964 | Kosik, Jr. |
| 3,254,111 A | 5/1966 | Hawkins et al. |
| 3,260,637 A | 7/1966 | von Bramer |
| 3,282,773 A | 11/1966 | Wicker, Jr. et al. |
| 3,324,855 A | 6/1967 | Heimlich |
| 3,393,962 A | 7/1968 | Andrews |
| 3,451,538 A | 6/1969 | Trementozzi |
| 3,523,628 A | 8/1970 | Colvin et al. |
| 3,524,537 A | 8/1970 | Winter |
| 3,527,224 A | 9/1970 | Rabinowitz |
| 3,527,841 A | 9/1970 | Wicker, Jr. et al. |
| 3,540,577 A | 11/1970 | Trementozzi et al. |
| 3,564,078 A | 2/1971 | Wicker, Jr. et al. |
| 3,579,628 A | 5/1971 | Gander et al. |
| 3,607,542 A | 9/1971 | Leonard et al. |
| 3,614,245 A | 10/1971 | Schwartzman |
| 3,667,472 A | 6/1972 | Halpern |
| 3,692,752 A | 9/1972 | Setsuda et al. |
| 3,742,018 A | 6/1973 | O'Sullivan |
| 3,779,706 A | 12/1973 | Nablo |
| 3,797,706 A | 3/1974 | Mule |
| 3,836,377 A | 9/1974 | Delahunty |
| 3,863,014 A | 1/1975 | Mottus |
| 3,903,055 A | 9/1975 | Buck |
| 3,924,623 A | 12/1975 | Avery |
| 3,941,488 A | 3/1976 | Maxwell |
| 3,975,422 A | 8/1976 | Buck |
| 3,995,641 A | 12/1976 | Kronenthal et al. |
| 4,003,942 A | 1/1977 | Buck |
| 4,012,402 A | 3/1977 | Buck |
| 4,013,703 A | 3/1977 | Buck |
| 4,038,345 A | 7/1977 | O'Sullivan et al. |
| 4,041,063 A | 8/1977 | Buck |
| 4,042,442 A | 8/1977 | Dombroski et al. |
| 4,057,535 A | 11/1977 | Lipatova et al. |
| 4,102,945 A | 7/1978 | Gleave |
| 4,105,715 A | 8/1978 | Gleave |
| 4,109,037 A | 8/1978 | Nohara |
| 4,142,630 A | 3/1979 | Hayes et al. |
| 4,170,585 A | 10/1979 | Motegi et al. |
| 4,171,416 A | 10/1979 | Motegi et al. |
| 4,182,823 A | 1/1980 | Schoenberg |
| 4,265,948 A | 5/1981 | Hayes et al. |
| 4,310,509 A | 1/1982 | Berglund et al. |
| 4,323,557 A | 4/1982 | Rosso et al. |
| 4,328,170 A | 5/1982 | Okawara et al. |
| 4,340,043 A | 7/1982 | Seymour |
| 4,364,876 A | 12/1982 | Kimura et al. |
| 4,374,126 A | 2/1983 | Cardarelli et al. |
| 4,377,490 A | 3/1983 | Shiraishi et al. |

(Continued)

FOREIGN PATENT DOCUMENTS

| DE | 2 261 261 | 7/1973 |
|---|---|---|
| DE | 40 09 621 | 10/1991 |

(Continued)

OTHER PUBLICATIONS

"Aclar®/Barex® Laminates: Flexible Solutions for Pharma Packaging" Drug Delivery Technology vol. 3, No. 3, May 2003, Posted on Mar. 28, 2008, http://www.drugdeliverytech.com/ME2/dirmod.asp?sid=&nm=&type=Publishing
&mod=Publications%3A%3AArticle
&mid=8F3A7027421841978F18BE895F87F791&tier=4
&id=6EC6964EB29D46D8A297E499E57A4164.

Borrel et al. "The Effect of Crown Ethers, Tetraalkylammonioum Salts, and Polyoxyethylene Amphiphiles on Pirarubicin Incorporation in K562 Resistant Cells" Biochemical Pharmacology, vol. 50, No. 12., pp. 2069-2076, 1995.

Cameron, J.L. et al., "The Degradation of Cyanoacrylate Tissue Adhesive, pt. 1", Surgery, vol. 58, Iss. 2, Aug. 1965, pp. 424-430.

Collins et al., "Biological Substrates and Cure Rates of Cyanoacrylate Tissue Adhesives" Archives of Surgery vol. 93, Sep. 1966, 428-432.

(Continued)

*Primary Examiner* — David J Blanchard
*Assistant Examiner* — Daniel F Coughlin
(74) *Attorney, Agent, or Firm* — Stradley Ronon Stevens & Young, LLP

(57) ABSTRACT

The invention relates to methods of using compositions for forming microbial sealant drapes. In particular, the invention relates to the use of compositions of combinations of cyanoacrylates for the in situ formation of drapes that can be used in surgery to protect patients from surgical site infections.

15 Claims, 1 Drawing Sheet

(56) References Cited

U.S. PATENT DOCUMENTS

| | | |
|---|---|---|
| 4,386,193 A | 5/1983 | Reich et al. |
| 4,413,753 A | 11/1983 | Stock |
| 4,439,196 A | 3/1984 | Higuchi |
| 4,444,933 A | 4/1984 | Columbus et al. |
| 4,447,224 A | 5/1984 | DeCant, Jr. et al. |
| 4,447,233 A | 5/1984 | Mayfield |
| 4,460,759 A | 7/1984 | Robins |
| 4,475,916 A | 10/1984 | Himmelstein |
| 4,480,940 A | 11/1984 | Woodruff |
| 4,486,194 A | 12/1984 | Ferrara |
| 4,487,603 A | 12/1984 | Harris |
| 4,533,422 A | 8/1985 | Litke |
| 4,542,012 A | 9/1985 | Dell |
| 4,551,366 A | 11/1985 | Maruhashi et al. |
| 4,554,686 A | 11/1985 | Baker |
| 4,643,181 A | 2/1987 | Brown |
| 4,646,765 A | 3/1987 | Cooper et al. |
| 4,649,909 A | 3/1987 | Thompson |
| 4,652,763 A | 3/1987 | Nablo |
| 4,685,591 A | 8/1987 | Schaefer et al. |
| 4,713,235 A | 12/1987 | Krall |
| 4,718,966 A | 1/1988 | Harris et al. |
| 4,772,148 A | 9/1988 | Buschemeyer |
| 4,786,534 A | 11/1988 | Aiken |
| 4,818,325 A | 4/1989 | Hiraiwa et al. |
| 4,925,678 A | 5/1990 | Ranney |
| 4,959,217 A | 9/1990 | Sanders et al. |
| 4,977,892 A | 12/1990 | Ewall |
| 4,978,527 A | 12/1990 | Brink et al. |
| 4,994,542 A | 2/1991 | Matsuda et al. |
| 5,009,654 A | 4/1991 | Minshall et al. |
| 5,039,753 A | 8/1991 | Woods et al. |
| 5,042,690 A | 8/1991 | O'Meara |
| 5,051,256 A | 9/1991 | Barnes |
| 5,069,907 A | 12/1991 | Mixon et al. |
| 5,083,685 A | 1/1992 | Amemiya et al. |
| 5,131,777 A | 7/1992 | Kimura et al. |
| 5,135,964 A | 8/1992 | Lee et al. |
| 5,167,616 A | 12/1992 | Haak et al. |
| 5,169,383 A | 12/1992 | Gyory et al. |
| 5,192,536 A | 3/1993 | Huprich |
| 5,225,182 A | 7/1993 | Sharma |
| 5,232,774 A | 8/1993 | Otsuka et al. |
| 5,236,703 A | 8/1993 | Usala |
| 5,240,525 A | 8/1993 | Percec et al. |
| 5,254,132 A | 10/1993 | Barley et al. |
| 5,283,034 A | 2/1994 | Okrongly et al. |
| 5,288,159 A | 2/1994 | Wirt |
| 5,302,629 A | 4/1994 | Berejka |
| 5,306,490 A | 4/1994 | Barley, Jr. |
| 5,312,864 A | 5/1994 | Wenz et al. |
| 5,328,687 A | 7/1994 | Leung et al. |
| 5,344,670 A | 9/1994 | Palmer et al. |
| 5,350,798 A | 9/1994 | Linden et al. |
| 5,358,349 A | 10/1994 | Burroughs et al. |
| 5,370,221 A | 12/1994 | Magnusson et al. |
| 5,403,591 A | 4/1995 | Tighe et al. |
| 5,411,345 A | 5/1995 | Ueji et al. |
| 5,453,457 A | 9/1995 | Meltzer et al. |
| 5,457,141 A | 10/1995 | Matsuda et al. |
| 5,470,597 A | 11/1995 | Mendenhall |
| 5,475,110 A | 12/1995 | Hudkins et al. |
| 5,480,935 A | 1/1996 | Greff et al. |
| 5,530,037 A | 6/1996 | McDonnell et al. |
| 5,547,662 A | 8/1996 | Khan et al. |
| 5,561,198 A | 10/1996 | Huver et al. |
| 5,665,817 A | 9/1997 | Greff et al. |
| 5,684,042 A | 11/1997 | Greff et al. |
| 5,730,994 A | 3/1998 | Askill et al. |
| 5,749,956 A | 5/1998 | Fisher et al. |
| 5,803,086 A | 9/1998 | Scholz et al. |
| 5,807,563 A | 9/1998 | Askill et al. |
| 5,874,044 A | 2/1999 | Kotzev |
| 5,902,594 A | 5/1999 | Greff et al. |
| 5,916,882 A | 6/1999 | Jeng |
| 5,928,611 A | 7/1999 | Leung |
| 5,944,754 A | 8/1999 | Vacanti |
| 5,957,877 A * | 9/1999 | Askill et al. .................... 602/54 |
| 5,979,450 A | 11/1999 | Baker et al. |
| 5,981,621 A | 11/1999 | Clark et al. |
| 5,985,395 A | 11/1999 | Comstock et al. |
| 5,998,472 A | 12/1999 | Berger et al. |
| 6,086,906 A | 7/2000 | Greff et al. |
| 6,090,397 A | 7/2000 | Lee et al. |
| 6,099,807 A | 8/2000 | Leung |
| 6,136,326 A | 10/2000 | Kotzev |
| 6,143,352 A | 11/2000 | Clark et al. |
| 6,143,805 A | 11/2000 | Hickey et al. |
| 6,155,265 A | 12/2000 | Hammerslag |
| 6,217,603 B1 | 4/2001 | Clark et al. |
| 6,228,354 B1 | 5/2001 | Jeng |
| 6,245,933 B1 | 6/2001 | Malofsky et al. |
| 6,248,800 B1 | 6/2001 | Greff et al. |
| 6,294,629 B1 | 9/2001 | O'Dwyer et al. |
| 6,299,631 B1 | 10/2001 | Shalaby |
| 6,310,166 B1 | 10/2001 | Hickey et al. |
| 6,323,275 B2 | 11/2001 | Takahashi et al. |
| 6,352,704 B1 | 3/2002 | Nicholson et al. |
| 6,488,665 B1 | 12/2002 | Severin et al. |
| 6,492,434 B1 | 12/2002 | Barley, Jr. et al. |
| 6,495,229 B1 | 12/2002 | Carte et al. |
| 6,547,917 B1 | 4/2003 | Misiak et al. |
| 6,579,469 B1 | 6/2003 | Nicholson et al. |
| 6,620,846 B1 | 9/2003 | Jonn et al. |
| 6,626,296 B1 | 9/2003 | Jimu et al. |
| 6,667,031 B2 | 12/2003 | Azevedo |
| 6,699,940 B2 | 3/2004 | Shalaby |
| 6,742,522 B1 | 6/2004 | Baker et al. |
| 6,743,858 B2 | 6/2004 | Hickey et al. |
| 6,746,667 B2 | 6/2004 | Badejo et al. |
| 6,767,552 B2 | 7/2004 | Narang |
| 6,779,657 B2 | 8/2004 | Mainwaring et al. |
| 6,797,107 B1 | 9/2004 | Kotzey |
| 6,802,416 B1 | 10/2004 | D'Alessio et al. |
| 6,849,082 B2 | 2/2005 | Azevedo |
| 6,881,421 B1 | 4/2005 | daSilveira et al. |
| 6,896,838 B2 | 5/2005 | D'Alessio |
| 6,942,875 B2 | 9/2005 | Hedgpeth |
| 6,960,040 B2 | 11/2005 | D'Alessio et al. |
| 6,974,585 B2 | 12/2005 | Askill |
| 6,977,278 B1 | 12/2005 | Misiak |
| 6,995,227 B2 | 2/2006 | Ryan et al. |
| 7,255,874 B1 | 8/2007 | Bobo et al. |
| 2002/0002223 A1 | 1/2002 | Cox et al. |
| 2002/0037272 A1 | 3/2002 | Askill et al. |
| 2003/0044380 A1 | 3/2003 | Zhu et al. |
| 2003/0077386 A1 | 4/2003 | Azevedo |
| 2003/0135016 A1 | 7/2003 | Tajima et al. |
| 2003/0149128 A1* | 8/2003 | Malofsky et al. .............. 523/111 |
| 2003/0158579 A1 | 8/2003 | Azevedo |
| 2003/0158580 A1 | 8/2003 | Azevedo |
| 2004/0115274 A1 | 6/2004 | Cox et al. |
| 2004/0120849 A1* | 6/2004 | Stewart et al. .................. 422/22 |
| 2004/0126355 A1 | 7/2004 | Childers |
| 2004/0127738 A1 | 7/2004 | Azevedo |
| 2004/0253039 A1 | 12/2004 | Stenton |
| 2005/0047846 A1 | 3/2005 | Narang et al. |
| 2005/0067312 A1 | 3/2005 | Gupta et al. |
| 2005/0142163 A1 | 6/2005 | Hunter et al. |
| 2005/0147582 A1 | 7/2005 | Zimmerman et al. |
| 2005/0182347 A1 | 8/2005 | Bishop et al. |
| 2005/0196431 A1 | 9/2005 | Narang et al. |
| 2005/0197421 A1 | 9/2005 | Loomis |
| 2005/0281866 A1 | 12/2005 | Jarrett et al. |
| 2005/0284487 A1 | 12/2005 | Gellerstedt et al. |
| 2006/0062687 A1 | 3/2006 | Morales |
| 2007/0041935 A1 | 2/2007 | Salamone et al. |
| 2007/0048356 A1 | 3/2007 | Schorr et al. |
| 2007/0078207 A1 | 4/2007 | Jonn et al. |
| 2007/0092481 A1 | 4/2007 | Misiak et al. |
| 2007/0092483 A1 | 4/2007 | Pollock |
| 2007/0147947 A1 | 6/2007 | Stenton et al. |
| 2008/0021139 A1 | 1/2008 | Blacklock et al. |
| 2008/0078413 A1 | 4/2008 | Padget et al. |

(56) References Cited

U.S. PATENT DOCUMENTS

| | | | |
|---|---|---|---|
| 2008/0102053 A1 | 5/2008 | Childers | |
| 2008/0319063 A1 | 12/2008 | Zhang | |
| 2009/0317353 A1 | 12/2009 | Zhang et al. | |
| 2010/0035997 A1* | 2/2010 | Broadley et al. | 514/635 |
| 2010/0269749 A1 | 10/2010 | Badejo et al. | |

FOREIGN PATENT DOCUMENTS

| | | |
|---|---|---|
| DE | 2010 3336 | 5/2001 |
| DE | 10 2007 019 044 | 10/2008 |
| EP | 0127466 | 12/1984 |
| EP | 0271675 | 6/1988 |
| FR | 2700698 | 7/1994 |
| GB | 1230560 | 5/1971 |
| GB | 2200124 | 7/1988 |
| JP | 59-066471 | 4/1984 |
| JP | 62-022877 | 1/1987 |
| JP | 03-207778 | 9/1991 |
| JP | 10-140091 | 5/1998 |
| WO | WO96/14292 | 5/1996 |
| WO | WO96/23532 | 8/1996 |
| WO | WO99/10020 | 3/1999 |
| WO | WO03/070257 | 8/2003 |
| WO | WO2004/045498 | 6/2004 |
| WO | WO2006/073922 | 7/2006 |
| WO | WO2009/003017 | 12/2008 |
| WO | WO2009/064291 | 5/2009 |

OTHER PUBLICATIONS

Darwish et al., "The evaluation of crown ether based niosomes as cation containing and cation sensitive drug delivery systems" International Journal of Pharmaceutics 159 (1997) 207-213.

Dumont et al., "New Oligosaccharidic Crown Ethers as Potential Drug-Targetting Vectors: Synthesis & Biological Evaluation" Bioorganic & Medicinal Chemistry Letters, vol. 4, No. 9, pp. 1123-1126, 1994.

Fussnegger, B. "Poloxamers (1) Lutrol® F 68 (Poloxamer 188)." BASF ExAct, Nov. 1999, 5-6.

Garnier-Suillerot et al., "Analysis of Drug Transport Kinetics in Multidrug-resistant Cells: Implications for Drug Action" Current Medicinal Chemistry, 2001, 8, 51-64.

Hansen, "Fast Cure—High moisture vapor transmission rate adhesives improve wound care." Adhesives Age Mar. 2003, 22, 24-25.

Lehman et al., "Toxicity of Alkyl 2-Cyanoacrylates", Archives of Surgery, vol. 93, Issue 3, Sep. 1966, pp. 441-446.

Leonard, F., "Hemostatic Applications of Alpha Cyanoacrylates: Bonding Mechanism and Physiological Degradation of Bonds", Adhesion in Biological Systems, ed. R.S. Manly, 1970, pp. 185-199.

Leonard, F. et al., "Interfacial Polymerization of n-Alkyl a-Cyanoacrylate Homologs", Journal of Applied Polymer Science, vol. 10 1966, pp. 1617-1623.

Leonard, F. et al., "Synthesis and Degradation of Poly (alkyl a-Cyanoacrylates)", Journal of Applied Polymer Science, vol. 10, Iss 8, Aug. 1966, p. 1214.

Leonard, F. et al., "Synthesis and Degradation of Poly(alkyl a-Cyanoacrylates)", Journal of Applied Polymer Science, vol. 10, Iss. 2, Feb. 1966, pp. 259-272.

Tseng, Y.C. et al., "Modification of synthesis and investigation of properties for 2-cyanoacrylates", Biomaterials, vol. 11, Jan. 1990, pp. 73-79.

Uchegbu et al., "Non-ionic surfactant based vesicles (niosomes) in drug delivery" International Journal of Pharmaceutics 172 (1998) 33-70.

Vezin, W.R. et al., "Diffusion of Small Molecules in Poly-n-Alkyl Cyanoacrylates", British Pharmaceutical Conference 1978—Communications presented at the 115th meeting, Coventry, Sep. 11-15, 1978, Journal of Pharmacy and Pharmacology, vol. 30, Issue: Suppl, Dec. 1978, p. 2P.

Vezin, W.R. et al., "In vitro heterogeneous degradation of poly(n-alkyl a-cyanoacrylates)", Journal of Biomedical Materials Research, vol. 14, 1980, pp. 93-106.

Woodward, S.C. et al., "Histotoxicity of Cyanoacrylate Tissue Adhesives in the Rat", Annals of Surgery, vol. 162, No. 1, Jul. 1965, pp. 113-122.

Yonezawa, M. et al., "Studies on a-Cyanoacrylate, VI: Reaction of Cyanoacetate with Formaldehyde" Yuki Gosei Kagaku Kyokaishi, vol. 25, Iss 4, Apr. 1967, pp. 311-316.

International Search Report and Written Opinion dated Dec. 8, 2010 for international application No. PCT/US2009/062761.

Material Safety Data Sheet (MSDS) of 2-octyl cyanoacrylate; Jun. 2, 2004.

Material Safety Data Sheet (MSDS) of isobuthyl-2-cyanoacrylate; Sep. 25, 1998.

Material Safety Data Sheet (MSDS) of n-butyl cyanoacrylate; Oct. 19, 2009 and Jun. 2, 2004.

Canale, A.J., et al., "Methyl a-cyanoacrylate. I. Free-radical homopolymerization", Journal of Applied Polymer Science, vol. 4, No. 11, Sep./Oct. 1960, pp. 231-236 [Abstract Only].

Quinn, J.V., "Clinical Approaches to the Use of Cyanoacrylate Tissue Adhesives", Tissue Adhesives in Clinical Medicine, Second Edition, 2005, BC Decker, Inc., pp. 27-76.

* cited by examiner

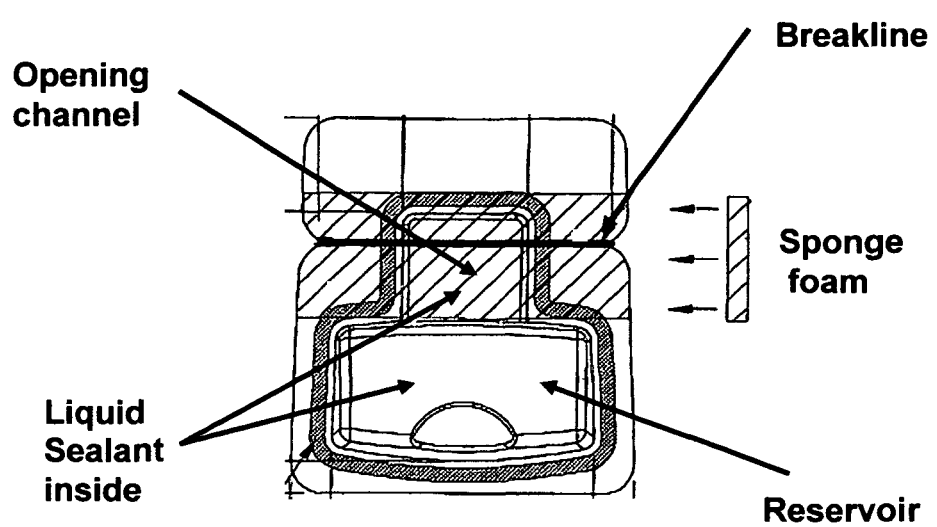

CYANOACRYLATE-BASED LIQUID MICROBIAL SEALANT DRAPE

CROSS REFERENCE TO RELATED APPLICATIONS

This application claims priority to the filing date of U.S. Provisional Application No. 61/197,954 filed Oct. 31, 2008; the disclosure of which is herein incorporated by reference.

BACKGROUND OF THE INVENTION

1. Field of the invention

The invention relates to methods of using compositions for forming microbial sealant drapes. In particular, the invention relates to the use of compositions of combinations of cyanoacrylates for the in situ formation of microbial sealant drapes that can be used in surgery to protect patients from surgical site infections.

2. Description of the Prior Art

Surgical site infections (SSIs) can be classified into two categories: (1) incisional and (2) organ, which includes organs and spaces manipulated during an operation. Incisional infections are further divided into superficial infections and deep soft tissue-muscle and fascia infections. The Centers for Disease Control and Prevention estimates that approximately 500,000 surgical site infections occur among an estimated 27 million surgical procedures conducted every year in the United States. Surgical site infections (SSI) are listed as the second most common cause of nosocomial infection after urinary tract infections, which accounts for 40% of hospital-acquired infections among surgical patients. Twenty five to thirty-eight percent of all nosocomial infections among surgical patients are estimated to be incisional surgical site infections. SSI is a significant cause of surgical morbidity and mortality, occurring in 2-5% of patients having clean extra-abdominal operations and up to 20% of patients undergoing intra-abdominal procedures. Patients with SSI are twice as likely to die, 60% more likely to be admitted to an Intensive Care Unit, and more than 5 times more likely to be readmitted to the hospital than patients who are not infected. Surgical site infections result in longer hospitalization and have large economic impact on patients and the health care system. Patients with surgical site infections are hospitalized an additional 7 days on average. The longer hospital stay cost an additional $3,152 on average. The average total cost for medical care during the eight weeks after hospital discharge is $5,155 for patients with surgical site infections compared with $1,773 for patients without SSIs. The total cost includes out patient visits, pharmacy, radiology services, re-hospitalization, skill-nursing facility, home health aids, and durable equipment.

The frequency of surgical site infections in patients varies from surgeon to surgeon, hospital to hospital, surgical procedure to surgical procedure and patient to patient. Surgical site infections can be caused by external sources of contamination including surgical personnel, surgical environment, and surgical instruments. Most SSIs are, however, caused by patient's own normal skin flora which can enter the body through the surgical incision. The patient's skin flora is considered as the first and foremost pathogenic source because the transmission of bacteria from skin to the incision is very efficient. Innocuous bacterial flora on the skin may also be colonized by pathogenic organisms. The bacteria of normal skin flora can cause wound infection in the presence of foreign materials that greatly enhance the pathogenic potential of these bacteria. Therefore, bacterial contamination occurs predominantly during and following surgical procedures.

Different methods of preventing SSIs have been developed to reduce patients' surgical site infections. Advanced surgical techniques and skillful surgeons can reduce the duration of surgery. Operation personnel and operation room hygiene management can lower the probability of exogenous pathogens. Operations that are conducted when patients have healthy physical and psychological states may enhance patients' immune system so that the chance of surgical infections may be considerably reduced. Thoughtful plans and careful selection of effective antibiotics can also help reduce the chance of contamination of bacteria.

Topical bactericidally active or antimicrobial agents such as iodophors, chlorhexidine, and alcohol-containing products have been applied to the surgical site before surgery to kill bacteria. These agents are preoperative skin preparation products, washes, surgical scrub tissues, wound cleaners, lotions and ointments. As early as 1960s, the successful use of prophylactic antibiotics was reported in a randomized, prospective, placebo-controlled clinical study of abdominal operations on the gastrointestinal tract. The success of antibiotic prophylaxis was due to the appropriate patient selection and wise choice of available agents.

U.S. Pat. No. 4,542,012 teaches the application of antimicrobial agents by depositing antimicrobial compositions onto human skin to form an antiseptic film. The antimicrobial composition is applied to the skin as a liquid solution in a fugitive solvent. After the solvent evaporates, a thin film containing antimicrobial agent is formed on the skin.

U.S. Pat. No. 5,916,882 discloses a providone-iodine alcohol gel antimicrobial skin-preparation formulation which is used to disinfect a surgical site. The pre-operative skin-preparation formulation quickly kills bacteria when applied to the surgical site. The skin-preparation formulation continues to effectively inhibit microorganism growth in the applied area for a relatively long period of time. Application of the skin-preparation formulation is controllable because the formulation does not run when applied to a patient. The antimicrobial skin-preparation formula includes iodine, alcohol and gel.

U.S. Pat. No. 6,228,354 provides a skin-preparation composition which does not harm the skin yet promotes asepsis on the skin. The skin-preparation composition disclosed has a rapid antimicrobial activity when in a liquid form and a sustained antimicrobial activity when dry. The skin preparation composition forms a water-resistant film on skin and is not readily removed when a wound or surgical site is sponged or irrigated. The antimicrobial film can be removed by rubbing an aqueous solution having the proper pH onto the skin. This patent describes a film-forming topical antimicrobial composition that includes a broad spectrum antimicrobial agent, a water-resistant polymer system, a neutralizer, a pH sensitive polymer, and an alcohol.

U.S. Pat. No. 6,488,665 discloses an antimicrobial skin-preparation delivery system used to disinfect a surgical site. The antimicrobial skin-preparation formula consists of iodine, alcohol and gel. The delivery system is composed of an antimicrobial alcohol gel formulation contained within a sealed, flexible container and a gel formulation dispenser connected to the container. A porous applicator pad with enlarged holes for passage of the gel formulation is described. The flow rate of the gel formulation is controlled by the external pressure applied to the flexible container.

US Patent Publication Nos. 20040126355 and 20080102053 disclose antimicrobial skin compositions comprised of an antimicrobial agent, water, an alcohol, and one or more pH sensitive viscosity builders. The composition's viscosity is from 100 cp to 1,000 cp and the formulation combines the advantages of an antimicrobial agent and an alcohol. The viscosity of the formulation permits dispensing from the applicator, while preventing the solution from flowing away from the wound area. pH sensitive methacrylic polymers are used as viscosity modifiers. The preparation forms a water-resistant film that is difficult to remove during wound irrigation, but can be easily removed upon completion of the procedure.

One of the disadvantages associated with topical application of skin preparation products is that the antimicrobial agents are only effective for a short period of time. Bacteria that may have survived the initial application of skin preparation products can proliferate and produce a large pathogen population. In addition, appropriate antimicrobial prophylaxis is determined by many factors such as proper case selection, anti-microbial agent selection, dosing and route of administration and duration of therapy. Inappropriate use of antimicrobial agents not only increases the cost of medical health care, but also exposes the patient to potential toxicity and other risks. Moreover, many gram-positive organisms isolated from patients with surgical site infections are resistant to multiple antimicrobial agents. The problem of antimicrobial resistance in gram-positive nosocomial pathogens has been a growing concern.

In addition to the use of antimicrobial skin preparation products, surgical incise drapes have also been used to help reduce the migration of germs and bacteria into the incision site. The surgical incise drape is usually a clear polymeric film with an adhesive backing on one side which is in turn covered with a release liner. Generally, the incise drape is used in conjunction with towels or surgical drapes to maintain the surgical site as sterile and clean as possible in order to inhibit surgical site infections. A continuous or longer lasting antimicrobial effect may be obtained by combining the antimicrobial agent with a surgical incise drape.

U.S. Pat. No. 3,579,628 discloses a hydrophilic acrylic film dressing which contains a composition which reacts with water to generate a bacteriostatic substance. The hydrophilic acrylic films are particularly suitable for use as occlusive dressings and for reducing bacteria.

U.S. Pat. Nos. 4,310,509 and 4,323,557 disclose dermatologically acceptable compositions made of a pressure-sensitive surgical incise drape and a broad-spectrum antimicrobial agent which can be released from the drape placed in contact with the skin. The active broad-spectrum antimicrobial agent is polyvinylpyrrolidone-iodine complex or chlorhexidine. The antimicrobial agents are applied onto the surgical drape which is made of polymeric materials such as polyurethane, polyvinyl ethers, polyesters, or polyethylene.

U.S. Pat. No. 4,340,043 discloses an adhesive-coated incise drape material incorporating uniform amounts of silver sulfadiazine as an antimicrobial agent. The incise drape is made of polyurethane sheets with an adhesive layer.

U.S. Pat. No. 4,643,181 discloses a surgical dressing or incise drape material comprising a substrate coated with an antimicrobial containing adhesive. The substrate may be a woven or knitted fabric, a nonwoven fabric, a plastic or a polymeric film. The preferred substrate in the invention is a polyurethane film. The antimicrobial is polyhexamethylene biguanide hydrochloride, which is distributed in the adhesive as particles with a size in the range of 20 to 300 microns.

U.S. Pat. No. 5,069,907 discloses a synthetic polymeric film or fabric surgical drape having incorporated therein a broad spectrum antimicrobial agent. The drape may have an adhesive layer attached to one of its external surfaces. The preferred antimicrobial agent used is 5-chloro-2-(2,4-dichloro-phenyl)phenol. Suitable adhesives utilized include polyacrylate adhesives.

U.S. Pat. No. 5,803,086 discloses adhesive coated incise drapes useful in surgical procedures. The incise drapes comprise a flexible film backed coating on one side with a dermatologically acceptable pressure sensitive adhesive (PSA) on the other side. The incise drape can be applied by two people wherein one person holds the core and a second person unrolls the drape by pulling on the handle protruding from the opposite end of the drape.

U.S. Pat. Nos. 5,979,450; 5,985,395 and 6,742,522 provide surgical incise drapes comprising a flexible film having a major portion thereof coated with an adhesive. The incise drape has a leading edge and a trailing edge and further includes a film handle at the leading edge. Methods described include providing a drape, grasping the film handle of the drape, pulling upon the liner to remove at least a portion of the liner exposing at least a portion of the adhesive coating the major portion of the flexible film, holding the surgical incise drape in a position such that at least a portion of the adhesive is contacting the patient, and then removing portions of the liner remaining.

US Patent Publication Nos. 20020002223, 20040115274 and 20080078413 disclose adhesive compositions containing acrylic polymers, tackifiers and a broad spectrum antimicrobial agent. The adhesive composition is an essentially solventless composition. The antimicrobial agent utilized is diiodomethyl-p-tolylsulfone with a preferred concentration of antimicrobial agents in the adhesive of about 0.1% to about 2% loading by weight. The antimicrobial adhesive composition is included in a polymeric substrate to form a surgical drape. The polymeric substrate is preferably a polyester or co-polyester sheet material.

US Patent Publication No. 20050284487 discloses a draping product, which is coated with adhesive along at least one edge. The adherence strength of the adhesive is greater than 0.5 N/25 mm when applied to skin. The damage to stratum corneum of the skin covered by the adhesive is less than 30% after removal. The adhesive coating is comprised of a pressure sensitive adhesive such as silicone elastomer, a hydrogel or a soft, tacky hot melt adhesive.

US Patent Publication No. 20070048356 describes an antimicrobial material composition that can be applied to material substrates. The antimicrobial composition includes a first or primary antimicrobial agent, such as polyhexamethylene biguanide (PHMB), a second antimicrobial agent, an antistatic agent or fluoropolymer and/or an organic acid. The substrate may encompass both woven and nonwoven fabrics made from either natural or synthetic fibers, rubber, plastic, and other synthetic polymer materials. The composition exhibits an effective microbe-killing efficacy within a period of about 30 minutes.

In spite of the beneficial properties of conventional surgical drapes with respect to inhibition bacterial infection, there are many challenges and problems associated with the conventional surgical drapes regardless of whether they incorporate antimicrobial agents. Under certain circumstances conventional surgical drapes may actually increase the risk of surgical site infection. Conventional surgical drapes can be lifted during surgery which results in entry of bacteria into the surgical site. The lifting of the conventional surgical drape is usually caused by failure of the adhesive to remain in contact with the patient's skin. Attempts to increase adhesive strength may also prove disadvantageous because more force is then required to remove the drape from skin leading to damage of the skin near the surgical site.

Conventional surgical drapes are normally large and difficult to apply to the patient without wrinkling the drape film. Wrinkling of the surgical drape at the surgical site may block visibility, making it difficult for the surgeon to see the incision site. In addition, the surgical drape will not prevent microorganisms from entering the incision if the drape is wrinkled. Wrinkling is especially problematic with application of the conventional surgical drapes to a non-flat skin surface such as the elbow or knee.

Incorporation of antimicrobial agents into conventional surgical drapes may permit the antimicrobial action of the agents to last longer. Antimicrobial agents currently available are, however, not effective at killing and immobilizing pathogens on the surface to which the agents are applied. The extensive use of antimicrobial products has raised concerns about antimicrobial resistance to antibiotics. In addition, most antimicrobial compounds are heat labile and cannot survive radiation sterilization. This makes it difficult to prepare sterile surgical drapes infused with antimicrobial agents.

Even though many different procedures have been applied to reduce surgical site infections, the risk of such infections still exists because of the continuing survival of skin bacteria after these treatments. Since endogenous flora on patient's skin plays a key role in the development of surgical site infections, a simple and comprehensive solution to the problem would be to minimize endogenous bacteria at and around the surgical site. It is known that cyanoacrylate polymer film can act as a mechanical barrier to penetration by bacteria while maintaining a natural healing environment. Cyanoacrylate monomers, which polymerize on contact with tissue surface to provide a thin and flexible polymer film, have been used as tissue adhesives for several decades. Cyanoacrylate adhesives also exhibit strong bond strength and very rapid cure time.

Cyanoacrylate' properties as adhesives may also make them desirable candidates as microbial sealant drapes. Cyanoacrylate microbial sealant drapes could prevent surgical site infections by overcoming the difficulties experienced by the conventional surgical drapes. U.S. Pat. No. 7,255,874 discloses that modified cyanoacrylate monomers can be used in various medical applications including wound closure, treatment of burns and abrasion and as surgical drapes. U.S. Pat. No. 5,730,994 describes methods for draping a surgical site by the in situ formation of cyanoacrylate polymer drape over skin surface. While the specification describes various cyanoacrylate monomers that can be used as surgical drapes, the preferred compositions contained only n-butyl cyanoacrylate. Furthermore, only n-butyl cyanoacrylate compositions were tested as surgical drapes.

There are several shortcomings associated with using n-butyl cyanoacrylate as a surgical drape. Compared to longer chain alkyl cyanoacrylates, n-butyl cyanoacrylate is less flexible and cracks more easily after forming a polymer film. Thus a plasticizer is usually needed in the n-butyl cyanoacrylate formulation to improve flexibility. In addition, short-chain cyanoacrylates polymerize quickly and then degrade rapidly into formaldehyde and the corresponding alkyl cyanoacetate, which can cause significant histotoxicity. Polymer films of n-butyl cyanoacrylate sloughs off from skin faster than that of long alkyl chain cyanoacrylates. Skin irritation also occurs with the use of n-butyl cyanoacrylate.

Hence, development of a cyanoacrylate-based microbial sealant drape which can immobilize the infectious microorganisms and effectively seal out the bacteria from a surgical site is desired. It is desirable to have a cyanoacrylate-based microbial sealantdrape product that can provide a uniform and flexible film. It is also desirable to develop a cyanoacrylate microbial sealant drape with significantly less tissue toxicity. Additionally, it is also desirable to develop an easy to use cyanoacrylate-based microbial sealant drape that will last a long time after the surgery to inhibit the postoperative surgical site infections.

SUMMARY OF THE INVENTION

The present invention provides cyanoacrylate-based liquid microbial sealant drape compositions comprising mixtures of cyanoacrylates to inhibit the surgical site infections. The liquid sealant film formed upon polymerization of the cyanoacrylate mixture prevents the spread of bacteria by trapping and immobilizing the microorganisms on the surgical sites. The compositions of the present invention provide flexible microbial sealant drapes without the addition of plasticizers and/or antimicrobial agents.

The present invention provides a method of performing surgery with a lowered risk of contamination including the steps of applying a preoperative skin preparation to a surgical site, applying the microbial sealant drape composition based on liquid cyanoacrylates to the surgical site, forming the microbial sealant film on the surgical site, making an incision through the microbial sealant film, and performing surgery.

The present invention provides liquid microbial sealant drape compositions which can effectively reduce the amount of microorganisms in the surgical site. Effective immobilization of microorganisms, by liquid microbial sealants of the present invention, were confirmed by both in vitro and in vivo bacteria immobilization test. In vitro immobilization test on sterile pig skin confirms that the microbial sealant compositions of the present invention are at least 95% effective in preventing the spread of the clinically relevant bacteria on the surgical sites under a variety of usage conditions. In preferred embodiments of the microbial sealant compositions of the present invention the compositions are at least 99.5% effective in preventing the spread of the clinically relevant bacteria on the surgical sites under a variety of usage conditions. In more preferred embodiments of the microbial sealant compositions of the present invention the compositions are at least 99.9% effective in preventing the spread of the clinically relevant bacteria on the surgical sites under a variety of usage conditions. The microbial sealant compositions of the present invention do not need to be used in combination with an antimicrobial surgical incise drape and may be used as a substitute for an antimicrobial surgical incise drape. The in vivo bacteria immobilization on 60 human subjects indicates that the microbial sealant compositions of the present invention can reduce microbial colonization by at least 99.9% within 15 minutes and maintain at least a 99.9% reduction throughout the 24 hours post treatment.

The present invention provides microbial sealant drape compositions which are resistant to the passage of blood-borne pathogens using viral penetration as a test system. No viral penetration was detected for the disclosed microbial sealant film.

The present invention provides a method of inhibiting the surgical site infections during and post the surgery. It takes days for the microbial sealant film to slough off. The disclosed cyanoacrylate liquid drape compositions are thus providing the post-surgical infection protection based on the anti-microbial property of cyanoacrylates.

The present invention provides microbial sealant drape compositions which provide a desirable degradation profile.

The present invention provides microbial sealant drape compositions including at least one cyanoacrylate monomer with longer alkyl chain and at least one cyanoacrylate monomer with shorter alkyl chain. The desired cyanoacrylate properties can thus be fine-tuned by combining the longer chain and shorter chain cyanoacrylates in specific ratios. Properties such as bonding strength, setting time, viscosity, degradability and biocompatibility can be altered depending on the specific combination of cyanoacrylates. Mixed cyanoacrylate compositions with about 60% to about 90% or more of 2-octyl cyanoacrylate are preferred for use as microbial sealants to prevent the surgical site infections.

The present invention provides sterile microbial sealant drape compositions which may be sterilized by the combination of ethylene oxide exposure and E-beam irradiation. Sterile microbial sealant compositions sterilized in this manner provide at least a two year shelf life.

The present invention provides microbial sealant drape compositions based on mixed cyanoacrylate monomers, which are packaged in a single use applicator. The applicator includes a compartment containing the microbial sealant composition as well as a sponge applicator tip. Cyanoacrylate-based microbial sealant composition can be readily dispensed onto the sponge applicator tip. A uniform sealing film can be formed by applying the cyanoacrylate-saturated sponge tip onto the surgical sites.

The present invention provides microbial sealant drape compositions which are compatible with currently available skin preparation products, surgical incise drapes and wound closure products.

The present invention provides microbial sealant drape compositions, which form flexible and tight films on the substrates so that little or no detectable cyanoacrylate residue is transferred into the incision wound by the surgical blade.

The present invention provides microbial sealant drape compositions which generate less heat during the application compared to commercially available drape products comprised of 100% butyl cyanoacrylate. The average temperature increase of the skin after applying microbial sealant composition of the present invention is no more than about 0.25° C.

The present invention provides microbial sealant drape compositions which provide a high flashpoint for safe use in the operating room or clinical surgery suite. The flashpoint for the disclosed microbial sealant composition is greater than 240° F. which is greater than 100% butyl cyanoacrylate drape products.

The present invention provides cyanoacrylate-based microbial sealant drape compositions which form a thin and uniform drape film on the surgical sites. The film thickness of the disclosed cyanoacrylate liquid drape compositions was evaluated using optical microscope, which is less than 500 μm.

The present invention provides cyanoacrylate-based microbial sealant drape compositions which has a desirable surface coverage. The average surface coverage of the drape composition disclosed in the present invention device was approximately 222.0 inch$^2$. The average surface coverage of the drape composition disclosed in the present invention device is much larger than that of the commercial applicators with the same amount of the liquid sealant.

The present invention provides cyanoacrylate-based microbial sealant drape compositions which are compatible with lasers. The microbial sealant films do not ignite, crack, blister or peel under the intense thermal energy of the lasers so that the microbial sealant film maintains its integrity and effectiveness as a sealant on the surgical site.

The present invention provides microbial sealant drape compositions which are compatible with defibrillators and electrocautery. The combined use of the disclosed microbial sealant composition with defibrillator and electrocautery does not affect the effectiveness of these devices. The disclosed microbial sealant composition demonstrates desirable performance with regard to charring, plume discoloration and cleaning of the blade upon completion of the incision and coagulation procedures. No signs of ignition, blistering, cracking or peeling were observed.

The present invention provides cyanoacrylate-based microbial sealant drape films which provides more resistance to water penetration by impact than the commercial cyanoacrylate films. The microbial sealant composition of the present invention elicited a mean value of 0.03 grams from penetration of water by impact compared to a mean value of 0.07 grams for butyl cyanoacrylate microbial sealant drapes.

The present invention provides microbial sealant drape compositions which are less irritating to the skin of a patient than prior art compositions. Based on the skin irritation study, the primary irritation index for the disclosed microbial sealant composition was calculated to be 0.7, while the primary irritation index for butyl cyanoacrylate drapes was calculated to be 1.4.

The present invention provides microbial sealant drape compositions which are safe and biocompatible. Cytotoxicity, genotoxicity, local irritation after implantation, and delay-type hypersensitivity of the disclosed microbial sealant compositions were evaluated based on ISO 10993, which confirmed the disclosed compositions are safe to be used as microbial sealant to inhibit the surgical site infections.

BRIEF DESCRIPTION OF THE FIGURES

FIG. 1 is an illustration of a preferred embodiment of the applicator for the cyanoacrylate microbial sealant drape compositions.

DETAILED DESCRIPTION OF THE INVENTION

The present invention provides compositions comprising sterile mixtures of cyanoacrylates with different length alkyl chains for use as a liquid microbial sealant drape that can inhibit the surgical site infections. The drape film formed upon polymerization of the mixture of cyanoacrylates prevents the spread of microorganisms by trapping or immobilizing bacteria that survive on patient's skin after common skin preparation procedures.

Preferred microbial sealant drape compositions disclosed herein include at least one cyanoacrylate with longer alkyl chain and at least one cyanocrylate with shorter alkyl chain. The longer alkyl chain cyanoacrylates are those containing 5 or more carbon atoms in the alkyl group, which include but are not limited to n-pentyl cyanoacrylate, iso-pentyl cyanoacrylate, n-hexyl cyanoacrylate, iso-hexyl cyanoacrylate, n-heptyl cyanoacrylate, 2-ethylhexyl cyanoacrylate, n-octyl cyanoacrylate, 2-octyl cyanoacrylate, nonyl cyanoacrylate, and decyl cyanoacrylate. The shorter alkyl chain cyanoacrylates are those containing 4 or less carbon atoms in the alkyl group, which include but are not limited to methyl cyanoacrylate, ethyl cyanoacrylate, n-propyl cyanoacrylate, isopropyl cyanoacrylate, n-butyl cyanoacrylate, isobutyl cyanoacrylate, 3-acetoxypropyl cyanoacrylate, 2-methoxypropyl cyanoacrylate, and 3-chloropropyl cyanoacrylate.

Varying the composition ratio of cyanoacrylate with different alkyl chains allows modification of the properties of cyanoacrylate compositions so that bonding strength, flexibility, cure time, degradability and biocompatibility can be controlled. Cyanoacrylates with long alkyl chains lacking oxygen-containing functional groups tend to form polymers that degrade slowly. Compared to longer chain cyanoacrylates, the shorter cyanoacrylate monomers have a higher degree of tissue toxicity due to their rapid degradation into formaldehyde and the corresponding cyanoacetate. Polymer films comprising longer alkyl chain cyanoacrylate tend to be more flexible than those made of shorter alkyl chain cyanoacrylates. Shorter alkyl chain cyanoacrylates have advantageous properties as tissue adhesives. For example, shorter alkyl chain cyanoacrylates provide faster curing speed and stronger bond strength as compared to longer alkyl chain cyanoacrylates.

In a preferred embodiment of compositions of the present invention, liquid microbial sealant drape compositions comprise 2-octylcyanoacrylate (OCA) in combination with n-butyl cyanoacrylate (BCA). In order to investigate the stability of the mixture of 2-octyl cyanoacrylate and n-butyl cyanoacrylate, a series of mixed cyanoacrylate compositions with different ratio of OCA/BCA were prepared and subjected to sterilization. Sterilization of the compositions is a requirement for their use as microbial sealants. Therefore it is important that the compositions can be sterilized without significant viscosity change. The compositions tested were composed of cyanoacrylates having the following ratios of n-butyl cyanoacrylate to 2-octyl cyanoacrylate: 10:90, 20:80, 30:70, 40:60, 50:50, 60:40, 70:30, 80:20 and 90:10. Table 1 shows the viscosity of the 2-octyl cyanoacrylate and n-butyl cyanoacrylate mixtures before and after the E-beam sterilization. The compositions were sterilized in HDPE bottles (1 ounce). Viscosity change correlates with the stability of cyanoacrylate monomers, stability being an important criterion for selecting the appropriate cyanoacrylate mixture compositions for use as microbial sealants. As shown in Table 1, E-beam sterilization has different effects on different mixtures of 2-octyl cyanoacrylate and n-butyl cyanoacrylate depending on the ratio of the two cyanoacrylates. The viscosity of the different compositions before the sterilization ranges from 3.68 to 3.88 cps and the difference is within the measurement accuracy of the viscometer. Mixed cyanoacrylate compositions having approximately 60% to about 90% 2-octyl cyanoacrylate demonstrate slight viscosity increases after E-beam sterilization. The preferred range of viscosity change is approximately 0% to 200%. The viscosity of the mixed cyanoacrylate compositions having about 50% or less of 2-octyl cyanoacrylate increases dramatically after the E-beam sterilization. This is indicative of instability of those compositions after undergoing E-beam sterilization. Mixed cyanoacrylate compositions having about 20% or less of 2-octyl cyanoacrylate cured after the E-beam sterilization and are unsuitable for microbial sealant compositions. In a more preferred embodiment of compositions of the present invention, compositions with about 60% to about 90% of 2-octyl cyanoacrylate are used as the liquid microbial sealant to prevent the surgical site infections. More preferably, compositions with about 70% to about 90% of 2-octyl cyanoacrylate are used. Even more preferably, compositions with about 80% of 2-octyl cyanoacrylate and about 20% of n-butyl cyanoacrylate is used as the liquid microbial sealant to prevent the surgical site infections.

TABLE 1

Viscosity of mixed OCA/BCA compositions before and after E-beam sterilization.

| | | Average viscosity (cps) | |
|---|---|---|---|
| Formulation | Composition | Before Sterilization | After Sterilization |
| 1a | 1:9 BCA/OCA | 3.68 | 5.11 |
| 1b | 2:8 BCA/OCA | 3.68 | 5.71 |
| 1c | 3:7 BCA/OCA | 3.68 | 5.11 |
| 1d | 4:6 BCA/OCA | 3.88 | 6.95 |
| 1e | 5:5 BCA/OCA | 3.88 | 15.77 |
| 1f | 6:4 BCA/OCA | 3.88 | 68.03 |
| 1g | 7:3 BCA/OCA | 3.68 | 505.63 |
| 1h | 8:2 BCA/OCA | 3.68 | Cured |
| 1i | 9:1 BCA/OCA | 3.68 | Cured |

In preferred embodiments of the present invention the liquid microbial sealant drape compositions provide at least two-year shelf life. The stability of the sterile cyanoacrylate adhesive compositions has evaluated by the accelerated aging. The accelerated aging test of the mixed cyanoacrylate microbial sealant composition was performed in an oven at 80° C. for a period of 12 days. The investigated compositions were tested for viscosity at intervals of 3, 6, 9 and 12 days. Based on ASTM F1980-2, 12 days accelerated aging at 80° C. correlates to 2 years of shelf life at ambient temperatures. Table 2 shows the viscosity of a sterile microbial sealant composition in an applicator containing 80% of 2-octyl cyanoacrylate and 20% of n-butyl cyanaocrylate at day 0, 3, 6, 9 and 12 of the accelerated aging at 80° C. The viscosity of the cyanoacrylate-based microbial sealant compositions increases as the accelerated aging proceeds but the increased viscosity of the aged samples at day 12 does not affect the performance of liquid drape compositions nor the dispensing of the compositions from the applicator.

TABLE 2

Viscosity of the sterile microbial sealant drape composition before and after the accelerated aging at 80° C. for 12 days.

| | Viscosity (cps) | | | |
|---|---|---|---|---|
| | Test 1 | Test 2 | Test 3 | Average |
| Day 0 | 4.29 | 3.68 | 3.06 | 3.68 |
| Day 3 | 4.29 | 3.68 | 4.90 | 4.29 |
| Day 6 | 4.90 | 4.90 | 5.52 | 5.11 |
| Day 9 | 6.13 | 6.13 | 6.74 | 6.33 |
| Day 12 | 27.0 | 25.7 | 30.6 | 27.8 |

In preferred embodiments of the present invention the microbial sealant drape composition is packaged in a user-friendly, single use applicator. As shown in FIG. 1, the applicator comprises a compartment containing the mixed cyanoacrylate compositions and a sponge applicator tip through which the liquid drape compositions may be applied to the surgical site. The applicator compartment is preferably air and water tight with a sealing mechanism to prevent contamination to the mixed cyanoacrylate monomers inside. When the compartment is opened, the mixed cyanoacrylate liquid sealant is evenly distributed onto the sponge applicator tip. Cyanoacrylate liquid drape compositions can be easily dispensed onto the sponge from an applicator once the sponge connection is folded. A uniform sealing film is formed by applying the cyanoacrylate-saturated sponge tip onto surgical sites.

According to the present invention, the microbial sealant drape compositions of the present invention can effectively reduce the amount of microorganisms in the surgical site. In preferred embodiments the microbial sealant compositions are at least 99.9% effective in preventing the spread of the clinically relevant bacteria on the surgical sites under a variety of usage conditions. The in vitro immobilization of microorganisms by the microbial sealant compositions was evaluated using sterile pig skin incised with a sterile surgical scalpel. Microorganisms used to challenge the surgical site may include without limitation pathogenic gram negative bacteria, gram positive bacteria, yeast and *Corynebacterium* sp. The immobilization of microorganisms by the microbial sealant compositions of the present invention was evaluated under different conditions which included without limitation using the microbial sealant composition without incision, using the microbial sealant composition with incision, using the microbial sealant composition with incision and skin surgical preps, and using the microbial sealant composition with incision and surgical incise drapes.

The microbial sealant drape compositions of the present invention were effective in preventing the mitigation in the test organism on the surgical site. Complete effectiveness was manifest as greater than 3.9 log 10 mitigation in the case of *S. epidermidis*, MRSA, *Corynebacterium* species, *Pseudomonas aeruginosa* and greater than 4 log 10 mitigation for *Candida albicans*. The microbial sealant compositions do not have an adverse effect on the effectiveness of surgical preps. The microbial sealant compositions do not need to be used in combination with an antimicrobial surgical incise drape. Instead the microbial sealant compositions of the present invention may be used as a substitute for an antimicrobial surgical incise drape.

According to the present invention, the preferred microbial sealant drape compositions can reduce microbial colonization by at least 99.9% within 15 minutes of application and maintain at least a 99.9% reduction throughout the 24 hours post treatment According to the present invention, the microbial sealant drape compositions are resistant to the passage of blood-borne pathogens. Testing based on ASTM F1671 "Test Method for Resistance of Materials Used in Protective Clothing to Penetration by Blood-Borne Pathogens Using Phi-X174 Bacteriophage Penetration as a Test System" was conducted to demonstrate the pathogen resistance. The test results indicated that the disclosed microbial sealant film is resistant to the passage of blood-borne pathogens using a viral penetration as a test system.

Preferred microbial sealant drape compositions of the present invention generate less heat during the application compared to commercially available drape products. Polymerization of cyanoacrylate is an exothermic process. The amount of heat released during polymerization is related to the length of the alkyl chain of the cyanoacrylate. Cyanoacrylates with shorter length chains release more heat. Too much heat generated from the application of cyanoacrylates onto human skin makes the patient uncomfortable. The exothermic effect of microbial sealant product of the present invention and a commercially available product was evaluated using an Infrared Thermometer to measure the temperature change on human skin. The skin temperature of patients was measured before and after the application of the drape products onto human skin. The average temperature increase after applying microbial sealant composition disclosed in the present invention and a commercially available product were 0.25 and 0.41° C., respectively. The test results indicate that less heat is released from the application of the preferred composition disclosed in the present invention than that of a commercially available product.

According to the present invention, the microbial sealant drape compositions of the present invention have a high flashpoint for safe use in the operating room or clinical surgery suite. The test was performed in accordance with ASTM D56-05, ISO 3679:2004 determination of flashpoint-rapid equilibrium closed cup method. The flashpoint for the microbial sealant compositions of the present invention is greater than 240° F. The flashpoint of the 100% butyl cyanoacrylate microbial sealant compositions is about 227° F.

According to the present invention, no cyanoacrylate residue was detected on a surgical blade through which an incision was made on a substrate covered with a microbial sealant drape compositions disclosed herein. The detection limit of the test was 5 ppm. The residue analysis on a surgical blade confirmed that no detectable cyanoacrylate sealants were transferred into the incision wound site.

According to the present invention, the preferred microbial sealant drape compositions of the present invention provide a desirable degradation profile. The integrity (degradation over time) of the disclosed microbial sealant film was evaluated following topical application to the skin of three pigs and comparisons were made to commercially available drapes. The microbial sealant films applied at each application site were evaluated for degradation at approximately 8 hours after application, and 1, 2, 3, 4, 6, 8, 10, 12, 14, and 16 days after application. Degradation of both the disclosed microbial sealant film and the commercial product was evident by the first observation interval (8 hours after application). At this time, 2 out of 12 test sites with the disclosed microbial sealant film remained intact and 5 out of 12 sites with the predicate device were intact. When the study ended on day 16, the microbial sealant film of the present invention was partially present in 2 of the 12 sites, while the commercial product was absent from all 12 sites.

According to the present invention, the liquid microbial sealant compositions are compatible with currently available skin preparation products, surgical incise drape products and wound closure products. Compatibility with current products means that the application of the disclosed microbial sealant drape composition does not adversely affect the performance of wound closure products and surgical incise drapes. Skin preparation products that may be used in concert with the compositions of the present invention include without limitation Chloraprep, Duroprep, 10% Povidone iodine and Betadine. Duraprep is preoperative skin preparation product comprising iodine povacrylex and isopropyl alcohol. ChloraPrep is a rapid-acting, persistent, and broad-spectrum preoperative skin preparation product, which consists of 2% Chlorhexidine Gluconate in 70% isopropyl alcohol. Betadine is a consumer-available topical antiseptics containing 10% of povidone-iodine. Surgical incise drapes may also be used with the cyanoacrylate compositions of the present invention including without limitation 3M Steri-strip and Ioban 2. Steri-Strip is an antimicrobial skin closure product that is made of a porous, non-woven backing coated with a pressure-sensitive adhesive which contains iodophor and is reinforced with polyester filaments for improved strength. Ioban 2 is an antimicrobial surgical incise drape with an iodophor impregnated adhesive providing a sterile surface and antimicrobial activity throughout the procedure. The compatibility of the preferred liquid microbial sealant compositions with current commercial products used for preventing surgical site infections was investigated by observing the effect of the disclosed liquid drape product on the adhesion property of surgical incise drape in the absence and presence of different skin preparation products.

The liquid cyanoacrylate sealant compositions of the present invention are also compatible with currently available wound closure products. The wound closure products may include SurgiSeal, Dermabond and Steri-Strip. Dermabond is a liquid bonding adhesive that holds cuts, incisions and wounds together. SurgiSeal is cyanoacrylate-based topical skin adhesive for the closure of wound and incisions to provide a flexible, water-resistant, antimicrobial protective coating, which provides the optimal balance between bond strength and flexibility.

According to the present invention, the preferred liquid cyanoacrylate sealant drape composition is compatible with lasers. The lasers that may be used in concert with the compositions of the present invention include without limitation $CO_2$, Nd:YAG, and Diode. The disclosed microbial sealant is intended to be used after typical operative skin preparation prior to a surgical incision. Lasers may be required to be used for skin incision, ablation, or coagulation for a surgical procedure. The in vitro study was conducted to evaluate the effect of both free beam and contact use of the lasers on the disclosed microbial sealant film formed on pig skin. The combined use of a skin prep such as Betadine with the disclosed microbial sealant composition was also investigated using a Diode laser. The integrity of the disclosed microbial sealant film was evaluated by macroscopic observations for cracking, blistering and peeling. The intense thermal energy of the lasers was used to determine if the disclosed microbial sealant film would ignite. The results showed that the disclosed microbial sealant film did not ignite, crack, blister or peel for all three laser types when used with either free beam or contact thermal energy applications so that the microbial sealant maintains its integrity and effectiveness as a sealant for the surgical procedure. These same results were obtained when combined with the surgical skin preparation product when the Diode laser was used with either free beam or contact laser.

According to the present invention, the cyanoacrylate-based microbial sealant compositions are compatible with defibrillators and an electrocautery. The in vitro study was conducted on porcine skin to evaluate the effect of the microbial sealant compositions of the present invention on the performance of the defibrillator and electrocautery. The microbial sealant composition was applied onto porcine skin. A metal plate or probe was attached on the underneath side of the porcine skin to measure the voltage of the defibrillator. In order to evaluate the compatibility with Electrocautery, a commercially available Electrocautery device was used to make incisions and coagulations on the porcine skins covered with the disclosed microbial sealant film. The Electrocautery settings were made at 70 watts for both incision and coagulation. The single coat application of the microbial sealant compositions of the present invention did not significantly decrease the conductance of the energy being discharged from the defibrillator. There was no observation of ignition, blistering, cracking or peeling. When used with the electrocautery, the microbial sealant compositions demonstrated desirable performance with regard to charring, plume discoloration and cleaning of the blade upon completion of the incision and coagulation.

According to the present invention, the cyanoacrylate liquid drape compositions provide a thin and uniform film on the surgical sites. In preferred embodiments of the present invention the drape film has a thickness of from about 5 to about 400 µm. More preferably, the drape film provides a thickness of about 10 to 200 µm, more preferably from about 30 to 80 µm and still more preferably from about 50 to 60 µm. The film thickness study indicates the formation of thin and uniform films of the disclosed liquid drape compositions.

According to the present invention, the liquid microbial sealant drape compositions provide greater resistance to penetration of water by impact than the commercially available liquid drapes. The resistance of the microbial sealant compositions of the present invention to the penetration of water by impact was investigated according to the American Association of Textile Chemists and Colorists (AATCC) test method. A volume of water is allowed to spray against the taut surface of the disclosed microbial sealant film backed by a weighted blotter. The blotter was then reweighed to determine water penetration. The microbial sealant compositions of the present invention have an average value of 0.03 grams from penetration of water by impact compared to an average value of 0.07 grams for a commercial drape composition. The test results indicate that the disclosed microbial sealant composition provides twice more resistance to water penetration by impact than the commercial product.

According to the present invention, the cyanoacrylate liquid sealant drape compositions are safe and effective as a surgical sealant product useful for inhibiting surgical site infections. The safety and biocompatibility of the disclosed liquid drape composition has been evaluated based on the International Organization for Standardization (ISO) 10993, Biological Evaluation of Medical Devices. Cytotoxicity was measured on the preferred liquid microbial sealant composition using an in vitro biocompatibility study. The liquid microbial sealant compositions of the present invention are not cytotoxic. For comparison, the in vitro cytotoxicity of prior art device was also evaluated, which showed no evidence of causing cell lysis or toxicity.

According to the present invention, the preferred liquid cyanoacrylate-based microbial sealant drape composition is less irritating than the prior art device, which was confirmed by the primary skin irritation study and ISO intracutaneous study.

According to the present invention, the preferred liquid microbial sealant drape composition is not genotoxic. Bacterial reverse mutation test, mouse peripheral blood micronucleus study and in vitro chromosomal aberration study in mammalian cells confirmed that the compositions are not genotoxic.

The mixed cyanoacrylate compositions may be stabilized with a combination of free radical stabilizer and anionic stabilizer. In embodiments of the present invention, the preferred primary free radical stabilizer is butylated hydroxyl anisole (BHA). BHA is used in an amount of about 200 to about 15000 ppm, preferably about 1000 to about 10000 ppm, more preferably about 2000 to about 8000 ppm. Other free radical stabilizers that may be used include without limitation, hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3-methoxyphenol; 2-tert-butyl-4methoxyphenol; 2,2-methylene-bis-(4-methyl-6-tert-butylphenol).

In embodiments of the present invention, the preferred primary anionic stabilizer is sulfur dioxide in an amount of about 2 to about 500 ppm, preferably from about 10 ppm to about 200 ppm. The anionic stabilizer may be a very strong acid including without limitation perchloric acid, hydrochloric acid, hydrobromic acid, toluenesulfonic acid, fluorosulfonic acid, phosphoric acid, ortho, meta, or para-phosphoric acid, trichloroacetic acid, and sulfuric acid. The very strong acid may be used in an amount of 0 to about 250 ppm, preferably from about 5 ppm to 50 ppm. Preferably, the very strong acid stabilizer is sulfuric acid, phosphoric acid or perchloric acid.

According to the present invention, the cyanoacrylate-based microbial sealant drape compositions are sterilized for medical use. The sterilization can be accomplished by common techniques, and is preferably accomplished by methods including, but not limited to, chemical, physical, and irradiation methods. An example of a chemical method includes, but is not limited to, exposure to ethylene oxide. Examples of irradiation methods include, but are not limited to, gamma irradiation, electron beam irradiation (E-beam), and microwave irradiation.

In preferred embodiments of the present invention, E-beam is used to sterilize the cyanoacrylate-based microbial sealant compositions. The dose of E-beam irradiation applied should be sufficient enough to sterilize both the package and the adhesive inside. The E-beam irradiation may be in a dosage of from about 5 to 50 kGy, and more preferably from about 12 to about 25 kGy. E-beam irradiation is preferably conducted at ambient atmosphere conditions and the exposure time to the irradiation is preferably from about 1 to about 60 seconds, more preferably from about 10 seconds to 60 seconds.

In preferred embodiments of the present invention, the viscosity of the preferred cyanoacrylate-based microbial sealant composition changes upon the E-beam sterilization. The average viscosity of the preferred microbial sealant drape composition comprising 20% butyl cyanoacrylate and 80% octyl cyanoacrylate before sterilization is 3.68 cps. After the sealant composition is subjected to E-beam sterilization the viscosity was measured to be 5.71 cps. The prior art references indicate that E-beam sterilization can induce serious partial polymerization of cyanoacrylate, which would lead to a large increase in viscosity.

In order to reduce the bioburden, the cyanoacrylate-based microbial sealant drape compositions may be filtered through a 0.2 μm filter. The applicators with the overpack may also be sterilized with heat, ethylene oxide prior to the final E-beam irradiation.

The sterility of the cyanoacrylate-based microbial sealant drape compositions may be analyzed by Bacteriostasis and Fungistasis tests. In embodiments of the present invention, a Sterility Assurance Level (SAL) should be obtained at a minimum of $10^{-3}$, which means that the probability of a single unit being non-sterile after sterilization is 1 in 1000. In more preferred embodiments, the Sterility Assurance Level may be at least $10^{-6}$.

The following non-limiting examples are intended to further illustrate the present invention.

EXAMPLE 1

Setting Time Measurement

Pig skin (4×4 square inch) was prepared by wiping the surfaces of the skin with sterile gauze saturated with isopropanol. All oily substances were thereby removed from the pig skin. The surface was wiped with sterile gauze to remove the isopropanol. The applicator containing the microbial sealant composition was opened and adhesive was permitted to saturate the sponge applicator tip for about 10 seconds prior to application. A thin film was applied to the pig skin after which elapsed time was recorded by a stop watch. Set time was then recorded by stopping the clock when the film was dry as determined at the point where no liquid transfer occurred when the film was touched with a gloved finger.

EXAMPLE 2

Viscosity Measurement

The viscosity of the cyanoacrylate compositions were measured by the Brookfield DV-II+ viscometer. The spindle and cup were cleaned with acetone after each measurement. About 0.5 ml of the microbial sealant composition was put into the cup and the cup was brought into position and slowly secured with the retaining arm. The motor was turned on after the sample was equilibrated in the cup. The viscosity of the disclosed microbial sealant composition was measured in triplicate. Any residue was removed with acetone prior to next sample measurement.

EXAMPLE 3

Average Set Time and Viscosity for Cyanoacrylate Mixtures

To a polyethylene bottle equipped with a magnetic stir bar, 24 g of n-butyl cyanoacrylate (BCA) was mixed with 56 g of 2-octyl cyanoacrylate (OCA) at room temperature for 4 hours (Composition 1). To a polyethylene bottle equipped with a magnetic stir bar, 32 g of n-butyl cyanoacrylate (BCA) was mixed with 48 g of 2-octyl cyanoacrylate (OCA) at room temperature for 4 hours (Composition 2). 3 lbs of n-butyl cyanoacrylate (BCA) was mixed with 12 lbs of 2-octyl cyanoacrylate (OCA) in a plastic container at room temperature for 4 hours. A trace amount of D & C Violet #2 was included in BCA and OCA as the colorant (Composition 3). Each of the three compositions was tested for average set time and average viscosity, as shown in Table 3.

TABLE 3

Average viscosity and set time of the preferred microbial sealant compositions.

| Composition | Avg. set time | Avg. viscosity |
|---|---|---|
| Composition 1 | 24.5 s | 3.68 cps |
| Composition 2 | 27.8 s | 3.88 cps |
| Composition 3 | 22.3 s | 3.88 cps |

EXAMPLE 4

Effect of the Preferred Microbial Sealant Composition on the Wound Closure Strength of Steri-Strip A skin model was used to evaluate the effect of the disclosed microbial sealant drape composition on the wound closure strength of commonly used wound closure products, 3M Steri Strips. Three (3) pig skin squares of skin model were randomly assigned to each of the following: a) no preparation product (untreated); b) liquid microbial sealant alone; c) Chloraprep alone; d) liquid microbial sealant drape applied over Chlorprep; e) Duroprep alone; f) liquid microbial sealant drape applied over Duroprep; g) Betadine alone; and h) liquid microbial sealant drape applied over Betadine. Following preparation of the incision site with skin preparation products and/or the disclosed liquid microbial sealant drape, an incision was made in the middle of the pig skin. The incisions were then closed with different wound closure products. After wound closure, the pig skin incisions were pulled apart using a Mark-10 tensiometer at a speed of 25 mm/min to determine wound closure strength. The data is summarized in Table 4.

TABLE 4

The Average Force Required for Separating Wound Closure of Steri-Strip on a Skin Model

| Sample Name | Sample 1 (lb-min/ sq in) | Sample 2 (lb-min/ sq in) | Sample 3 (lb-min/ sq in) | Average Force (lb-min/ sq in) |
|---|---|---|---|---|
| Untreated | 3.0 | 3.2 | 3.2 | 3.13 |
| Liquid microbial sealant | 9.4 | 7.6 | 8.8 | 8.60 |
| Betadine | 1.6 | 1.8 | 1.2 | 1.53 |
| Betadine and Liquid mcirobial sealant | 8.2 | 7.6 | 6.2 | 7.33 |
| Chloraprep | 3.0 | 3.0 | 3.2 | 3.07 |
| Chloraprep and Liquid microbial sealant | 10.6 | 7.8 | 7.0 | 8.47 |
| Duraprep | 2.4 | 3.0 | 2.2 | 2.53 |
| Duraprep and Liquid microbial sealant | 9.0 | 12.2 | 10.8 | 10.67 |

EXAMPLE 5

Surface Coverage of the Disclosed Microbial Sealant Applicator

A liquid microbial sealant composition comprising 80% of 2-octyl cyanoacrylate and 20% of n-butyl cyanoacrylate was applied to pig skins from an applicator until all the adhesive (3.5 mL) was dispensed. The length and width of the covered areas was measured with electronic digital calipers. These values were used to calculate the surface coverage per applicator. The surface coverage was measured according to the following procedures. A 4×12 inch of pig skin was prepared by wiping the surfaces of the skin with sterile gauze saturated with isopropanol to make sure that all oily substances were removed from the pig skin. The surface of the skin was wiped dry with gauze. The microbial sealant composition was applied to the prepared pig skin until the entire adhesive in a single applicator was distributed (3.5 ml). The whole area of the pig skin was covered by diminishing the gap and overlap as much as possible and by keeping the strokes even. The width and length of pig skin covered with adhesive was measured using an electronic digital cather. The surface area was calculated from the measured width and length. The average surface coverage of the drape composition disclosed in the present invention device was approximately 222.0 inch$^2$.

EXAMPLE 6

Film Thickness

The drape film thickness was measured using optical microscopy. The drape film compositions comprising 80% of 2-octyl cyanoacrylate and 20% of n-butyl cyanoacrylate were prepared by applying the drape composition from the applicator onto two adjacent glass slides. The cyanoacrylate compositions were allowed to dry. A razor blade was used to make a cut between the two glass slides to create a cross section in the cured film that was approximately in line with the glass slide edges. The glass slide with the cured drape film was mounted with a clamp on the metallographic microscope such that the cross section of the slide and the cured film could be viewed by optical microscopy. The specimen was magnified with the 20× lens. A series of measurements of film thickness were made by comparing the images of the samples with a standard optical image photographed at the same camera and microscope settings. Three measurements per sample were made per photograph and three photographs were taken per film for a total of 9 measurements per film. Under the test condition, the microbial sealant film has a thickness of less than about 500 μm.

EXAMPLE 7

Cytotoxicity

Cytotoxicity was tested on a microbial drape composition comprising 80% of 2-octyl cyanoacrylate and 20% of n-butyl cyanoacrylate using an in vitro biocompatibility study based on ISO 10993, Part 5. The disclosed liquid drape composition was applied to both sides of a glass slide to cover an area 15 mm by 75 mm. The coated slides were allowed to dry prior to placing them into a container for extraction. The test article was extracted with a single strength Minimum Essential Medium (1×MEM) with 5% serum and 2% antibiotics. The test extract was placed onto three separate monolayers of L-929 mouse fibroblast cells propagated in 5% $CO_2$. High density polyethylene was used as the negative control and tin stabilized polyvinylchloride was used as the positive control. All monolayers were incubated at 37° C. in the presence of 5% $CO_2$ for 48 hours, which was then examined microscopically to determine any change in cell morphology. The liquid microbial sealant compositions of the present invention did not cause cell lysis or toxicity.

EXAMPLE 8

Genotoxicity Study I

A glass rod was cleaned with 70% isopropyl alcohol and allowed to air dry. The rod was then coated with a microbial sealant drape composition comprising 80% of 2-octyl cyanoacrylate and 20% of n-butyl cyanoacrylate up to 4 cm and allowed to dry for at least 1 minute prior to extraction with dimethyl sulfoxide (DMSO) and 0.9% sodium chloride at 37° C. for 72 hours. Another glass rod without cyanoacrylate liquid drape was similarly subjected to the extraction conditions for use as a negative control. Known mutagens, benzo[a]pyrene and 2-nitrofluorene, were used as positive control to demonstrate that tester strain TA 98 was sensitive to mutation reversion to wild type. For tester strains TA100 and TA 1535, sodium azide and 2-aminoanthracene were used as positive controls. For tester 1537, 2-aminoanthracene and ICR-191 were used as positive controls. For tester strain WP2uvrA, 2-aminoanthracene and methylmethane-sulfonate were used as positive controls.

Tubes containing molten top agar supplemented with tryptophan for the *Escherichia coli* or with histidine-biotin solution for the *Salmonella typhimurium* were inoculated with culture for each of the five tester strains and with the DMSO and saline extracts of the disclosed cyanoacrylate liquid drape film. Sterile water for injection (SWI) or S9 homogenate simulating metabolic activation was added as necessary. Tryptophan-free media plates (for *E. coli*) and histidine-free media plates (for *S. typhimurium*) were prepared in triplicate as follows: 1) DMSO and saline extracts of the cyanoacrylate liquid drape film with and without S9 activation; 2) negative controls with and without S9 activation; and 3) positive controls with different tester strains in the absence and presence of S9 activation.

The plates were incubated at 37° C. for 2 to 3 days. Following the incubation period, the revertant colonies on each plate were recorded. The mean number of revertants and standard deviation was determined. The mean number of revertants of the test plates was compared to the mean number of revertants of the negative control for each of the five tester strains. It was concluded that, under the study conditions, the disclosed liquid microbial sealant compositions in both DMSO and saline extracts were not mutagenic to *Salmonella Typhimurium* strains (TA98, TA100, TA1535, and TA1537), and were not mutagenic to tryptophan-dependent *Escherichia coli* strain WP2uvrA.

EXAMPLE 9

Genotoxicity Study II

A glass rod was cleaned with 70% isopropyl alcohol and allowed to air dry, and then coated with the microbial sealant drape compositions comprising 80% of 2-octyl cyanoacrylate and 20% of n-butyl cyanoacrylate up to 4 cm. The drape was allowed to dry for at least 1 minute prior to extraction with dimethyl sulfoxide (DMSO) and 0.9% sodium chloride at 37° C. for 72 hours. Additional test rods without cyanoacrylate microbial sealant were subjected to the same extraction conditions as the test article and were used as negative controls. Methyl methanesulfonate (MMS) in saline, an antineoplastic drug known to have mutagenic properties, was used as a positive control.

Five groups of mice, each of which consisted of 6 male and 6 female, were injected with cyanoacrylate liquid drape in SC extract, cyanoacrylate liquid drape in SO extract, negative control in SC, negative control in SO, and positive control with methyl methanesulfonate, respectively. Each mouse received an intraperitoneal injection at a dose of 20 ml/kg of the appropriate extract accordingly for consecutive three days. All animals were observed immediately following injection and on a daily basis to access general health. On day 4, blood was collected from the tail veins of each mouse and solutions were prepared. The normochromatic erythrocytes were evaluated for the presence of micronuclei. The frequency of micronucleated reticulocytes (MN-RETs) was determined and used as an index of genotoxicity. The frequency of reticulocytes relative to total erythrocytes was calculated as an indication of stem cell toxicity. Both SC and SO extracts of the cyanoacrylate liquid drapes of the present invention did not show statistically significant increases in the frequency of MN-RETs. Cyanoacrylate liquid microbial sealant compositions of the present invention are not genotoxic under the study conditions. Also, there was no evidence of cellular toxicity from extracts of the disclosed cyanoacrylate liquid drape composition.

EXAMPLE 10

Local Irritation and Toxicity Study

Local irritation or toxicity effect after implantation of the microbial sealant drape compositions comprising 80% of 2-octyl cyanoacrylate and 20% of n-butyl cyanoacrylate was conducted to evaluate the potential for a local irritant or toxic response to the drape implanted in direct contact with muscle tissue. High density polyethylene was used as the negative control. Three Albino New Zealand rabbits were used for the test. One incision was made on each side of the rabbit back. The fascia was cut to expose the paravertebral muscle. A pocket was formed with a hemostat between the muscle fibers into which the implant material was introduced. After four weeks, the rabbits were weighed and then euthanized by an intravenous injection of a sodium pentobarbital based drug. The paravertebral muscles were dissected free and fixed in 10% neutral buffered formalin to facilitate cutting. The tissue was macroscopically examined using low magnification to look for capsule formation or other signs of irritation. The excised sections were also histologically processed for microscopic evaluations. The disclosed microbial sealant drapes of the present invention caused no macroscopic reaction under the study conditions, while microscopic examination indicated the disclosed composition was moderately irritating to the tissue.

EXAMPLE 11

ISO Intracutaneous Study

Intracutaneous study of microbial sealant drape compositions comprising 80% of 2-octyl cyanoacrylate and 20% of n-butyl cyanoacrylate was conducted to determine whether leachables extracted from the disclosed microbial sealant composition wound cause local dermal irritant effects following injection into rabbit skin. The glass rods were wiped clean with 70% isopropyl alcohol and allowed to air dry. The glass rod was coated with the disclosed microbial sealant compositions up to 4 cm and allowed to air dry for at least one minute prior to placing in the extraction container. The test article was extracted in 0.9% sodium chloride USP solution (SC) and sesame oil, NF 9 (SO) at 37° C. for 72 hours. A 0.2 ml dose of the test article extract was injected by the intracutaneous route into five separate sites on the right side of the back of each rabbit. Injections were spaced approximately 2 cm apart. The appearance of each injection site was noted immediately after injection. Observations for erythema and edema were conducted at 24, 48, and 72 hours after injection. Under the conditions of this study, there was no erythema and no edema from the SC extract injected intracutaneously into rabbits. There was very slight erythema and very slight edema from the SO extracts injected intracutaneously into rabbits.

EXAMPLE 12

ISO Skin Irritation Study

Skin irritation study of cyanoacrylate-based microbial sealant drape compositions comprising 80% of 2-octyl cyanoacrylate and 20% of n-butyl cyanoacrylate was conducted to evaluate the potential for a single topical application of the disclosed microbial sealant composition to irritate skin. New Zealand white male rabbits were used for this study. On the day of treatment, four sites, two on each side of the back cranially and caudally, were designated on each rabbit. A 0.5 ml portion of the disclosed microbial sealant composition was applied topically to each cranial site by introduction under a 4 ply gauze layer to an area of skin approximately 25 mm×25 mm square. The patches were backed with plastic and covered with a nonreactive tape. After the 24 hour exposure, the binders, tape and patches were removed. The sites were graded for erytherma and edema at 1, 24, 48 and 72 hours after removal of the single sample application. Under the conditions of the study, very slight erythema and no edema were observed on the skin of the rabbits. The primary irritation index for the disclosed microbial sealant composition was calculated to be 0.7.

EXAMPLE 13

Residue Analysis

The residue analysis on surgical blade was determined on a pig skin model. A microbial sealant drape composition comprising 20% butyl cyanoacrylate and 80% octyl cyanoacrylate was applied to pig skin as the sealant before incision. An incision was made through the drape film using a surgical blade. The surgical blade was then immersed in HPLC grade acetone to extract any possible cyanoacrylate residue. The acetone solution after extraction was analyzed by GC/MS to determine if any residual cyanoacrylate was left on the blade after an incision was made. The fresh surgical blade cutting through pig skin without treatment by microbial sealants served as a negative control. Solution of polymer film of the preferred microbial sealant composition in acetone was used as the positive control to determine the detection limit of GC/MS.

In order to determine the limit of detection, positive controls were run and various peaks were compared to determine which peaks were best for assessing the presence of the materials. A peak associated with cyanoacrylate at 14.7 minutes was found to be best for quantification and detection of cyanoacrylate. At 5 ppm, the peak at 14.7 minutes for cyanoacrylate was observed clearly with a large ratio of signal/noise, which was thus assigned as the detection limit. Following the same condition used for the positive control, the residual analysis of surgical blade used to cut through the drape film of the preferred compositions in the present invention was conducted. No cyanoacrylate was detected indicating that no residue of the disclosed drape composition on surgical blade was found at the detection limit of 5 ppm. There was no cracking, blistering or flaking of the drape film observed when the incision was made on the microbial sealant of the preferred composition disclosed herein. These observations suggest that the microbial sealant compositions disclosed in the present invention provide the desirable flexibility and strong bonding strength.

EXAMPLE 14

Adhesion Properties

A pig skin model was used to evaluate the effect of the disclosed microbial sealant drape compositions on the adhesion property of the commonly used surgical incise drapes with and without the treatment of the skin preparation products. The following treatments were subjected to the pig skin model test: a) no preparation product (untreated); b) liquid microbial sealant alone; c) Chloraprep alone; d) liquid microbial sealant applied over Chlorprep; e) Duroprep alone; f) liquid microbial sealant applied over Duroprep; g) 10% Povidone Iodine alone; and h) liquid microbial sealant applied over 10% Povidone Iodine. The skin model was prepared by applying different skin preparation products and the liquid microbial sealant, after which a surgical incise drape such as 3M Steri-Strip and Ioban 2 was applied to the surface of each model. The surgical incise drape was then peeled away from the skin model using a Mark-10 tensiometer to determine the adhesion strength of the incise drape at a speed of 50 mm/min.

Table 5 shows the average force required to peel Steri-strip from the pig skin treated under various conditions. Compared to skin models untreated or treated only with skin preparation products, the adhesion strengths of Steri-Strip on skin models with the liquid microbial sealants of the present invention are 2-3 times greater. The test results demonstrate that the use of the disclosed liquid drape composition improves the adhesion strength of the commonly used surgical incise drapes. The surgical incise drape provides increased adhesion strength when applied to the substrates sequentially treated with the skin preparation products and the liquid microbial sealants compared to those applied to the substrates treated only with the skin preparation products. These observations indicate that the disclosed liquid microbial sealant is compatible with commercial surgical incise drapes and skin preparation products and provides increased adhesion strength.

TABLE 5

Average strength required to peel Steri-strip from the pig skin model

| Treatment | Average strength (lb/in$^2$) |
|---|---|
| Untreated | 0.67 |
| Liquid microbial sealant | 1.40 |
| A commercial liquid drape | 1.20 |
| Povidone iodine | 0.67 |
| Povidone iodine + liquid microbial sealant | 1.67 |
| Povidone iodine + a commercial liquid drape | 1.40 |
| Chloraprep | 0.67 |
| Chloraprep + liquid microbial sealant | 1.20 |
| Chloraprep + a commercial liquid drape | 1.20 |
| Duroprep | 0.53 |
| Duroprep + liquid microbial sealant | 1.67 |
| Duroprep + a commercial liquid drape | 1.33 |

EXAMPLE 15

Compatibility with Wound Closure

A pig skin model was used to evaluate the effect of the disclosed microbial sealant drape composition on the wound closure strength of the wound closure products with and without pre-treatment with skin preparation products. The testing skin models were randomly assigned to the following treatments: a) no preparation product (untreated); b) liquid cyanoacrylate microbial sealant alone; c) Chloraprep alone; d) liquid microbial sealant applied over Chlorprep; e) Duroprep alone; f) liquid cyanoacrylate microbial sealant applied over Duroprep; g) Betadine alone; and h) liquid cyanoacrylate microbial sealant applied over Betadine. Following preparation of the incision site with skin preparation products and/or the disclosed liquid microbial sealant, an incision was made in the middle of the pig skin. The incisions were then closed with different wound closure products. After wound closure, the pig skin incisions were pulled apart after 1-2 minutes using a Mark-10 tensiometer at a speed of 25 mm/min to determine the wound closure strength.

The average wound closure strength of SurgiSeal in the absence and presence of different skin preparation products and/or the liquid microbial sealant drape compositions of the present invention is summarized in Table 4. The disclosed liquid drape composition and different skin preparation products including Betadine, Chlorprep and Duraprep, were evaluated for the effect on the wound strength of SurgiSeal. As shown in Table 6, the wound closure strength of SurgiSeal in the presence of the liquid microbial sealant is slightly greater than that in the absence of the liquid microbial sealant. Likewise, the wound closure strength of other wound closure products such as Dermabond and Steri-strip is stronger liquid microbial sealant drapes of the present invention are applied as compared to that without applying the liquid cyanoacrylate microbial sealant. These observations indicate that the disclosed liquid cyanoacrylate microbial sealant is compatible with commercially available wound closure products and provides for improved closure strength.

TABLE 6

The Average Force Required for disrupting Wound Closure of SurgiSeal on a Skin Incision Model

| Treatment | Average strength (lb) |
| --- | --- |
| Untreated | 4.5 |
| Liquid microbial sealant | 8.9 |
| Betadine | 4.7 |
| Betadine + liquid microbial sealant | 6.9 |
| Chloraprep | 4.7 |
| Chloraprep + liquid microbial sealant | 5.9 |
| Duroprep | 4.8 |
| Duroprep + liquid microbial sealant | 6.1 |

EXAMPLE 16

Skin Irritation

Skin irritation study of a cyanoacrylate-based liquid microbial sealant drape compositions comprising 80% of 2-octyl cyanoacrylate and 20% of n-butyl cyanoacrylate was conducted to evaluate the potential for a single topical application of the disclosed microbial sealant composition to irritate skin. New Zealand white male rabbits were used for this study. Under the conditions of this study, very slight erythema and no edema were observed on the skin of the rabbits for the disclosed microbial sealant composition. The primary irritation index for the disclosed microbial sealant composition was calculated to be 0.7, while the primary irritation index for the predicate device was calculated to be 1.4.

EXAMPLE 17

Intracutaneous Study

Intracutaneous study of the microbial sealant drape compositions comprising 80% of 2-octyl cyanoacrylate and 20% of n-butyl cyanoacrylate was conducted to determine whether leachables extracted from the disclosed microbial sealant composition wound cause local dermal irritant effects following injection into rabbit skin. For comparison, the corresponding study was also conducted for a commercial liquid drape. The test article was extracted in 0.9% sodium chloride USP solution (SC) and sesame oil, NF 9 (SO). A 0.2 ml dose of the test article was injected by the intracutaneous route into five separate sites on the right side of the back of each rabbit. Observations for erythema and edema were conducted at 24, 48, and 72 hours after injection. As shown in Table 7, there was no erythema and no edema from the SC extract of the disclosed microbial sealant composition injected intracutaneously into rabbits. There was very slight erythema and very slight edema from the SO extract of the disclosed microbial sealant composition injected intracutaneously into rabbits with a mean difference score of 0.3. In comparison, there was well-defined to moderate erythema and well-defined to severe edema from the SO extract of a commercial liquid drape, injected intracutaneously into rabbits with a mean difference score of 2.1.

TABLE 7

Summary of ISO intracutaneous study

| Test article | Extract | Test group mean score | Control group mean score | Mean difference score (test − control) |
| --- | --- | --- | --- | --- |
| 20% BCA and 80% OCA | SC | 0.0 | 0.0 | 0.0 |
| | SO | 0.8 | 0.5 | 0.3 |
| A commercial liquid drape | SO | 2.6 | 0.5 | 2.1 |

| SCORE | ERYTHEMA | EDEMA |
| --- | --- | --- |
| 0 | No erythema | No edema |
| 1 | Very slight erythema (barely perceptible) | Very slight edema (barely perceptible) |
| 2 | Well-defined erythema | Well-defined edema (edges of area well-defined by definite raising) |
| 3 | Moderate erythema | Moderate edema (raised approximately 1 mm) |
| 4 | Severe erythema (beet redness) to eschar formation preventing grading of erythema | Severe edema (raised more than 1 mm, and extending beyond exposure area) |

EXAMPLE 18

In Vitro Bacteria Immobilization

Sterile pig skin, 4×4 inches, was aseptically cut into 4×1 cm pieces. Each piece of the sterile pig skin was inoculated with 0.1 mL (about 75,000 colony forming units) of MRSA, *S. epidermids, Pseudomonas aeruginosa, Candida albicans,* or *Corynebacterium* sp. to a marked 4×1 cm area of the skin. The incision site was defined by a metric ruler to the depth of the fat layer below the dermis and length of about 4 cm. The inoculated skin was placed under a laminar flow hood to allow the inoculum to dry at ambient laboratory temperature. A microbial sealant composition comprising 20% butyl cyanoacrylate and 80% octyl cyanoacrylate was then applied onto the inoculated skin over the incision site. An incision was then made with a sterile scalpel and the pig skin was manipulated by gently squeezing the incision site to simulate surgical trauma. Excess skin was cut away from the incision site with a sterile scalpel. To determine whether organism had migrated from the skin surface to the incision site, the incision site was irrigated with 0.1 mL of sterile elution fluid and the eluate was collected. Ten-fold serial dilutions of the eluate were prepared and duplicate pour plate counts and membrane filtration count were performed. The agar plates were incubated for 48 to 72 hours at 35-37° C. Analysis of data shows that the disclosed microbial sealant compositions were at least >99% effective in preventing the spread of the microorganisms into the wound site.

EXAMPLE 19

In Vivo Bacteria Immobilization

A total of 60 healthy volunteers (29 females and 31 males) were recruited to evaluate the in vivo bacteria immobilization of a microbial sealant composition comprising 20% butyl cyanoacrylate and 80% octyl cyanoacrylate. The study included a 14-day pretreatment washout period for stabilization of skin bacteria flora. During the washout period, subjects refrained from using any topical antimicrobials, systemic antibiotics, medical soaps, lotions, shampoos, etc, for at least two weeks before the evaluation and throughout the study. The tested area consisted of the right inguinal region. Hair was removed using a sterile disposable clipper device. A sterile drape was used to isolate the inguinal area from the rest of the body and then a surgical marker was used to draw four different 1 inch squares separated by 1 inch of normal skin in which the microbial sealant composition was applied. Using sterile gloves the products were applied onto the skin in its designated areas and allowed to dry. Sterile gauze was placed over the test area to avoid subsequent contamination. Swabbed samples from skin were collected at 15 minutes, 4 hours and 24 hours after the initial application of the microbial sealant composition. The sample collection procedure was performed using a sterile technique including sterile gloves, sterile microbial sealants, surgical masks and hats. After the sampling was completed the entire contents of the tube was poured carefully onto a 1 mL Petrifilm aerobic plate (plate count agar) and the plates were incubated for 48 hours at 30° C. 3M™ Petrifilm™ plate was used to quantify colony counts. At 15 minutes, the absolute log reduction was 5.568 for the disclosed microbial sealant composition. The absolute log reduction of bacteria for the disclosed microbial sealant composition is 4.299 and 3.33 at 4 hours and 24 hours, respectively.

EXAMPLE 20

In Vitro Chromosomal Aberration Study in Mammalian Cells

A chromosomal aberration study was conducted to determine whether an extract of the microbial sealant drape composition wound cause clastogenic changes in Chinese Hamster Ovary (CHO). A glass rod was sterilized with 70% isopropyl alcohol and allowed to air dry. The glass rod was then coated (4 cm) with a microbial sealant composition comprising 20% butyl cyanoacrylate and 80% octyl cyanoacrylate and allowed to air dry for at least 1 minute prior to placing the coated rod in the extraction container. A single preparation was extracted with DMSO with agitation at 37° C. for 72 hours. Following extraction, the DMSO extract was diluted with McCoy's 5A medium to a final concentration of 25% prior to testing. Aveclor 1254=induced rat liver (S9 homogenate) was used as metabolic activation. The S9 homogenate is prepared from male, Sprague Dawley rats. An uncoated glass rod was subjected to the same extraction conditions to serve as a negative control. A known direct acting genotoxic compound, Mitomycin C (MMC), was used as a positive control to demonstrate that CHO cells were sensitive to mutagens in the absence of metabolic activation. The microbial sealant composition extract, negative control, and positive control were tested in triplicate. For the assays conducted without metabolic activation, the growth medium in each of three test culture flasks was replaced with 10 ml of the prepared extracts. For the assay conducted with metabolic activation, the test samples were supplemented with isocitrate dehydrogenase (NADP+) at 60 μl/ml and S9 at 20 μl/ml. After 18 hours of incubation at 37° C. in the presence of $CO_2$, the medium was decanted and the cultures were rinsed twice with 4-6 ml of calcium magnesium free phosphate buffered saline (CMF-PBS). The flasks were incubated for an additional 2 hours at 37° C. After harvesting, slides of the cells were prepared, stained with Giemsa, and examined microscopically for chromosomal aberrations at 100× magnification. Under the conditions of this assay, the DMSO test extract of the disclosed microbial sealant composition was not considered genotoxic to Chinese Hamster Ovary cells in the absence of S9 metabolic activation. The prepared McCoy's extract was not considered genotoxic to Chinese Hamster Ovary cells in the presence or absence of S9 metabolic activation. The positive and negative controls performed as expected.

EXAMPLE 21

Resistance to Impact Penetration

The resistance of a microbial sealant drape composition comprising 20% butyl cyanoacrylate and 80% octyl cyanoacrylate to the penetration of water by impact was evaluated by following the American Association of Textile Chemists and Colorists (AATCC) test method. Test sample films of the microbial sealant composition were made that measured 178×230 mm. The samples and the blotting paper were conditioned in an atmosphere of 65±2% relative humidity (RH) at 21±1° C. for 4 hours before testing. After clamping the film onto an inclined stand, a standard blotter 152×230 mm was weighed and inserted beneath the test sample. A 500±10 ml volume of distilled water at 27±1° C. was poured into a funnel of the tester and allowed to spray onto the test sample of the microbial sealant composition. After the spraying, the test sample was carefully lifted, the blotter removed and reweighed to determine the amount of water that penetrated the film during the test. The mean value for the microbial sealant composition was 0.03 grams. Under the same conditions a commercial microbial sealant film comprised of 100% butyl cyanoacrylate displayed a mean value of 0.07 grams.

EXAMPLE 22

Sealant Film Integrity Over Time

The integrity (degradation over time) of a microbial sealant composition comprising 20% butyl cyanoacrylate and 80% octyl cyanoacrylate was evaluated following topical application to the skin of three pigs and compared to another microbial sealant product. The pigs were restrained in a sling for up to 30 minutes during the application procedures. To reduce possible stress at being restrained in the sling, the pigs were initially conditioned to the sling over the course of 3 days prior to commencement of the application procedures. The day prior to treatment, each pig was weighed and placed in a sling. The hair on the dorso-lateral area was removed. The depilated skin was washed with povidone iodine scrub, rinsed well with water, and dried. On the day of the application procedure, each pig was placed in a sling. The depilated area of the back was scrubbed with povidone iodine, wiped with 70% isopropyl alcohol and painted with 10% povidone iodine antiseptic. The microbial sealant composition of the present invention and another commercial drape were applied to four sites approximately 1×2 inches in area. The applied drape film at each application site was evaluated for degradation at approximately 8 hours after application, and 1, 2, 3, 4, 6, 8, 10, 12, 14, and 16 days after application. Degradation of both microbial sealant films was evident by the first observation interval (8 hours after application). At this time, 2 out of 12 test sites with the microbial sealant film of the present invention remained intact and 5 out of 12 sites with the commercial film were intact. When the study ended on day 16, the microbial sealant film of the present invention was partially present in only 2 of the 12 sites, while the commercial film was absent from all 12 sites.

What is claimed is:

1. A microbial sealant drape composition, comprising a mixture of about 80% by weight of monomeric 2-octyl cyanoacrylate, about 20% by weight of monomeric n-butyl cyanoacrylate, about 2000 ppm to about 8000 ppm of butylated hydroxyl anisole, and about 10 ppm to about 200 ppm of sulfur dioxide or about 5 ppm to about 50 ppm of an acid stabilizer selected from the group consisting of sulfuric acid, phosphoric acid, and perchloric acid, wherein the composition is sterilized by ethylene oxide exposure or irradiation, the viscosity of the composition increases no more than 200% after sterilization, and wherein the sterilized composition has at least two years of shelf stability as measured by an American Society for Testing and Materials (ASTM) accelerated aging standard, and wherein the composition does not contain any plasticizer or antimicrobial agent.

2. The microbial sealant drape composition of claim 1, wherein the composition, when applied to a surgical site, reduces microbial colonization of the surgical site by at least 99.9% within 15 minutes of being applied to the surgical site.

3. The microbial sealant drape composition of claim 1, wherein the composition, when applied to a surgical site, polymerizes into a film resistant to passage of viruses.

4. The microbial sealant drape composition of claim 1, wherein the composition, when applied to a surgical site, polymerizes into film having a thickness of about 50 to 60 μm.

5. The microbial sealant drape composition of claim 1, wherein the composition is compatible with skin preparation products, surgical incise drapes, and wound closure products.

6. The microbial sealant drape composition of claim 1, wherein the composition is compatible with lasers, defibrillators, and electrocautery equipment.

7. The microbial sealant drape composition of claim 1, wherein the composition is sterilized by Electron-beam (E-beam) irradiation.

8. The microbial sealant drape composition of claim 1, wherein the composition provides a surface coverage greater than 200 inch$^2$.

9. A method for reducing microbial colonization of a surgical site, comprising applying the microbial sealant drape composition of claim 1 to the surgical site.

10. The microbial sealant drape composition of claim 1, wherein the composition, when applied to a surgical site, does not increase the temperature of the skin at the surgical site to which the composition has been applied more than about 0.25° C.

11. The microbial sealant drape composition of claim 1, wherein the flashpoint of the microbial sealant drape composition is greater than 240° F.

12. The microbial sealant drape composition of claim 1, wherein the composition is bactericidal.

13. The microbial sealant drape composition of claim 1, wherein the composition is sterilized by irradiation.

14. The microbial sealant drape composition of claim 1, wherein the composition does not contain any plasticizer.

15. The microbial sealant drape composition of claim 1, wherein the ASTM accelerated aging standard is the ASTM F1980-02 standard.

* * * * *